United States Patent [19]

Cansell

[11] Patent Number: 4,825,871

[45] Date of Patent: May 2, 1989

[54] DEFIBRILLATING OR CARDIOVERTING ELECTRIC SHOCK SYSTEM INCLUDING ELECTRODES

[75] Inventor: Albert Cansell, Wissembourg, France

[73] Assignee: Societe Anonyme Dite: Atesys, Wissembourg, France

[21] Appl. No.: 54,095

[22] Filed: May 18, 1987

Related U.S. Application Data

[63] Continuation of Ser. No. 716,760, Mar. 27, 1985, abandoned.

[30] Foreign Application Priority Data

Mar. 27, 1984 [FR] France .................. 84 04751

[51] Int. Cl.⁴ .............................................. A61N 1/36
[52] U.S. Cl. .................................. 128/419 D; 128/786
[58] Field of Search ................... 128/419 D, 784–788

[56] References Cited

U.S. PATENT DOCUMENTS

| | | | |
|---|---|---|---|
| 3,614,955 | 10/1971 | Mirowski et al. | 128/419 D |
| 3,835,864 | 9/1974 | Rasor et al. | 128/785 |
| 3,857,398 | 12/1974 | Rubin | 128/419 D |
| 3,942,536 | 3/1976 | Mirowski et al. | 128/419 D |
| 3,995,623 | 12/1976 | Blake et al. | 128/419 P |
| 4,030,509 | 6/1977 | Heilman et al. | 128/419 D |
| 4,198,963 | 4/1980 | Barkalow et al. | 128/419 D |
| 4,210,149 | 7/1985 | Heilman et al. | 128/419 D |
| 4,291,699 | 9/1981 | Geddes et al. | 128/419 D |
| 4,291,707 | 9/1981 | Heilman et al. | 128/784 |
| 4,301,815 | 11/1981 | Doring | 128/786 |
| 4,407,303 | 10/1983 | Akerstrom | 128/786 |
| 4,475,551 | 10/1984 | Langer et al. | 128/419 D |

*Primary Examiner*—William E. Kamm
*Attorney, Agent, or Firm*—Schwartz & Weinrieb

[57] ABSTRACT

A device for a defibrillating or cardioverting electric shock to a patient for correcting securement tachyarrhythmias features of a catheter for insertion through the right atrium and into the right ventricle for locating a heartbeat sensor inside the heart and at least one discharge electrode in the right ventricle spaced from the interior surface of the heart, another discharge electrode external to the heart and circuitry connected by the catheter between the sensor and discharge electrodes for supplying electric shock to the discharge electrodes in response to a signal from the heartbeat sensor.

23 Claims, 2 Drawing Sheets

DEFIBRILLATING OR CARDIOVERTING ELECTRIC SHOCK SYSTEM INCLUDING ELECTRODES

This application is a continuation of application Ser. No. 716,760, filed on 3/27/85 now abandoned.

The present invention relates to apparatus designed to be partly or completely implanted in the body of a human or animal subject in order to deliver an electric shock to the heart of the subject whenever the heart goes into ventricular fibrillation or ventricular tachycardia or more generally to deal with disturbances of the cardiac rhythm by electrical means.

It is known that apparatus designed to remedy auriculoventricular blocks are cardiac stimulators which send impulses to the ventricles when the normal impulses can no longer arrive due to a fault in conduction of the bundle of His. These impulses consist of electric currents of a few volts and about 1 milliampere which are transmitted at the frequency of the normal heartbeat to a probe inside the right ventricle extending from the Vena Cava. The energy provided by this probe is extremely small since excitation of only a few cells of the right ventricle is sufficient for this excitation to be propagated throughout the cardiac muscle and cause its contraction. Ventricular fibrillation, on the other hand, poses a quite different problem and the energies required are much greater.

Ventricular fibrillation is in fact an anarchic excitation of most of the ventricular cells. In certain cases, a multiplicity of centres of excitation is produced in the tissue of the ventricles so that passage of the cells to the excited state does not take place in an orderly fashion and the ventricles cannot contract with the necessary amplitude. In other cases, a plurality of annular bands of contraction known as "re-entry circles" is formed. Supposing that an abnormal excitation known as an "extrasystole" appears over a zone of the ventricles, then this excitation is gradually transmitted along a closed annular path and the phenomenon becomes self-sustaining if the length of the loop, the speed of propagation of the excitation along the loop and the time required for the excitation of the cells to die down are such that the exctation front always encounters in front of it cells which have already returned to the de-energized state. This state of fibrillation is generally produced in a diseased heart when an extrasystole occurs during a vulnerable phase of the electrocardiogram or when an external shock, for example due to electrocution, occurs during this phase. As a result of this state of fibrillation, the ventricles no longer undergo orderly rhythmical contractions but only small vibrations and tremors of the cardiac wall so that the ventricles cease to pump blood and the pressure drops virtually instantly, leading to virtually complete cessation of the blood circulation of the subject. The subject falls almost instantly into a coma and death intervenes within a few minutes if the fibrillation of the heart cannot be stopped during this very short period of time.

It is well known that defibrillation may be achieved by applying metal discs externally to the skin of the subject on either side of the heart and transmitting an electric discharge of several hundred of joules to the discs. This discharge brings all the cardiac cells at once into the excited state so that the propagation of the excitation fronts along the re-entry circles is instantly stopped since these fronts encounter cells in the excited state and not in the de-energized state. The self-sustaining character of the state of fibrillation can thereby be eliminated so that the cardiac muscle can return to the normal state of beating in response to impulses transmitted to it by the natural cardiac stimulator situated in the right auricle. When the state of fibrillation is the result of an accident, it is not possible to foresee it and the subject therefore can only be saved by the external application of electrodes, provided this is carried out sufficiently rapidly. If, on the other hand, fibrillation is the result of a pathological state diagnosed by the cardiologist so that it can be foreseen that statistically the subject is under a high risk of going into fibrillation, then it becomes necessary to provide an automatic apparatus by which the defibrillation shock necessary at the moment when fibrillation occurs can be automatically applied to the heart.

A first type of such an apparatus, known as a MIROWSKI defibrillator, is based on the principle of using two electrodes, the first of which is introduced into the right ventricle on a catheter while the second is an epicardiac electrode consisting of a flexible metal wire placed on the apex of the heart. These two electrodes are connected to a circuit capable of delivering an electric discharge when it receives a control signal. This control signal is released by a detector circuit which is connected to a sensor and analyzes the electric signals supplied by the heart beats. This device is capable of effectively defibrillating a subject in ventricular fibrillation but it has a number of serious disadvantages. The first disadvantage is that the positioning of the electrode on the apex of the heart requires a major surgical operation, generally with thoracotomy. The second disadvantage is that the defibrillation shock requires a relatively large supply of energy although it already represents progress compared with the earlier systems of the "bipolar" type since in these systems the electric discharge was produced between two electrodes carried on the same catheter introduced into the Vena Cava, the right auricle and the right ventricle, one of the electrodes being at the base of the ventricle while the other was situated inside the Vena Cava. With such a system, the discharge preferentially acted on the right zone of the heart so that a much greater energy of discharge was required to act on the whole mass of the heart. This earlier system required discharge energies of at least 50 joule. Nevertheless, the Mirowski system still requires a relatively large amount of energy so that the amount of energy which can be stored is limited to that required for about a hundred discharges and the volume of the box containing the supply batteries and the electric circuit is relatively large, being of the order of 150 $cm^3$.

A third type of apparatus, which may be referred to as "unipolar", is distinguished from the above mentioned device by the fact that the second electrode, instead of being placed on the apex of the heart, is fitted to the outside of the thoracic cage, generally under the skin, and is therefore regarded as "inert" in contrast to the first electrode, which is situated in the right ventricle and which is the active discharge electrode.

In the practical embodiments of this last mentioned apparatus, however, as incidentally also in the previous devices, the two electrodes of the sensor are placed in the right ventricle. Now it has been found that when discharge takes place, the cardiac cells close to the electrode inside the heart are "deadened" for a significant length of time, of the order of one hour. The resulting modification of the electrocardiogram is known as "lesion wave". This means that the signals recorded after a discharge between the two electrodes of the sensor are completely deformed compared with the corresponding signals of a normally functioning heart so that the detector circuits are not capable of suitably registering a fresh state of fibrillation during the period of time that the cells adjacent to these two endocavitory electrodes remain in an abnormal state. Bearing in mind the characteristics of the detector circuit, it is even possible for a release of discharge to take place while the cardiac muscle is not in fibrillation.

According to a first aspect, the invention provides an improvement to the last mentioned system in overcoming this disadvantage by means of the fact that the discharge electrode of the right ventricle plays no role at all in picking up the signal which registers the heart function.

For this purpose, according to the invention, it is the inert electrode which constitutes one of the elements of the sensor while the other element is quite distinct from the discharge electrode inside the cardiac cavity.

As a result, the electric signals recorded between the two elements of the sensor act on cells which are not "deadened" by the discharge. This ensures complete reliability of the apparatus since the signal recording the heart function is in no way deformed, not even just after discharge. Furthermore, since the apparatus according to the invention carries out a unipolar defibrillation, that is to say with a single electrode inside the cardiac cavity, its discharge is capable of affecting the entire mass of the heart since the inert electrode is sufficiently far away from the heart to ensure that the flow lines of the currents of discharge will not have any preferential direction. Since blood is a good conductor, the discharge pole corresponding to the endocavitory electrode is distributed over the whole internal wall of the cardiac muscle while the other pole is connected to the cardiac tissue by the tissue of the human or animal body interposed between the inert electrode and the heart. It is, of course, possible to use a plurality of inert electrodes for the apparatus according to the invention in order to improve the distribution of the lines of flow of the discharge current so that the whole cardiac mass will be involved.

According to a second aspect of the invention, a flexible spacer device capable of contracting on introduction of the catheter is associated with the endocavitory discharge electrode in order to isolate this electrode from the wall of the cardiac muscle to prevent any preferential passage of the discharge to any one wall and ensure good distribution over all the walls by virtue of the good conductivity of the blood. The advantages which flow from this arrangement are a considerable reduction in the energy required both for defibrillation and for cardioversion, whether the current be applied in the bipolar mode in relation to an identical, second electrode or in relation to one or more inert electrodes placed on or under the skin.

The invention thus essentially provides an electrode combined with an element of an elastic insulating material capable of contracting at the moment when the electrode is introduced into the heart or extracted from the heart and of expanding after said introduction so as to ensure that the conductive part of the electrode will be separated and/or isolated from the internal wall of the heart. According to a first variation, this element is separate from the electrode itself and consists of a crown of radial petals forming an integral part of the catheter upstream and/or downstream of the said ring and set at a sufficient angle in relation to the axis of the catheter to ensure the desired separation of the catheter from the heart wall when expanded and capable of folding itself back elastically towards the axis to enable the catheter to be introduced or withdrawn. According to a second variation, it constitutes the actual support of the electrode which consists of a metallization of this support on the side opposite to the heart wall, as will be explained in more detail hereinafter.

It should be noted that the apparatus according to the invention may be adapted for the purpose of cardioversion, that is to say the treatment of ventricular tachycardia. It is known that this heart disorder is of the same type as fibrillation but less serious. In ventricular tachycardia, annular bands of abnormal contraction are again found on the heart but these re-entry circles are less numerous so that the ventricles can continue to contract although to an insufficient extent. In other words, ventricular tachycardia generally only affects a reduced mass of the ventricles so that the defibrillation energy required to stop the abnormal functioning may be considerably less, for example, amounting to only 1/10 to 1/1000 of the energy required to stop ventricular fibrillation. The shock of cardioversion is generally synchronized with the ventricular complex. The form of electrocardiogram signals obtained in the case of ventricular tachycardia is very different from that obtained in the case of ventricular fibrillation and consequently the detector circuit combined with the sensor of the apparatus according to the invention can easily distinguish between the two signals. In the case of ventricular fibrillation, the patient is comatose and it therefore causes no discomfort to transmit a discharge which affects the skeletal muscles, as does a discharge between an inert electrode and an endocavitory electrode. In ventricular tachycardia, on the other hand, the patient is conscious and it is preferable to avoid a shock affecting the skeletal muscles. In that case, it is sufficient to provide a specific electrode on the catheter of the apparatus according to the invention and to pass the discharge between this third electrode and the electrode in the right ventricle, which forms one of the poles of the discharge in the case of ventricular fibrillation. The apparatus according to the invention can therefore intervene in ventricular tachycardia by sending a discharge between two endocavitory electrodes and thus avoid any shock to the skeletal muscles. Bearing in mind the arrangement of the two electrodes on the same catheter, it will be evident, as already indicated, that the lines of current flow of the discharge will preferentially affect the right side of the heart. In order to affect the whole mass of the heart, it would therefore be necessary to increase the energy of discharge beyond that which would be necessary if the discharge were produced by means of an inert electrode placed at some distance from the heart. This increase in energy, however, causes no difficulty since only a low level of energy is required for overcoming ventricular tachycardia. Due to this low level of energy, the cells in the vicinity of this third electrode which is specific to ventricular tachycardia will obviously not be "deadened" at the moment of discharge, and this additional electrode may therefore be used as sensor element.

The primary object of the present invention is therefore the novel industrial product constituting a cardiac defibrillator of the type comprising, firstly, a cardiac signal sensor having at least two elements, the said sensor being connected to a detector circuit, and secondly, a first discharge electrode connected to one of the poles of an electric discharge circuit controlled by the aforesaid detector circuit, the said first discharge electrode being mounted on a catheter which is introduced into the right ventricle of the heart, and thirdly, at least one second discharge electrode known as "inert" electrode, connected to the other pole of the discharge circuit and external to the heart, characterised by the fact that the second discharge electrode or electrodes at the same time constitutes or constitute the first element of the sensor, the second element of said sensor being distinct from the first discharge electrode.

In a preferred embodiment, the first discharge electrode takes the form of a conductive element such as a metal ring mounted on the endocavitory catheter and associated with a spacer element made of a material preventing its mechanical and/or electric contact with the cardiac wall.

According to a first variation, this spacer element consists of a plurality of petals of a plastics material arranged round the catheter and substantially perpendicular to the axis of the catheter, the said petals separating the first discharge electrode from the internal wall of the heart muscle. Such a device may be placed upstream or downstream of the discharge electrode or both.

According to a second variation, this element consists of a rectangular band of plastics material such as ethylene polyterephthalate, for example of the quality sold under the Trade Mark "MYLAR", fixed to the catheter along one small side and wrapped round itself in a spiral so that after it has been introduced, the turns of the spiral expand elastically and their end portion can come into contact with the heart wall.

In this second variation, it is important to note that the spacer element has the particular characteristic of presenting a surface of contact with the blood and/or cardiac tissues which is greater than the developed surface of the conductive metal ring, so that efficient electric insulation and mechanical separation from the heart wall is obtained.

In the case of metallization of this spacer element, the metallization may cover only the central zone of said internal surface in order to ensure that the edge of the band will not be conductive. This embodiment enables the electrode to be used for treating classical defibrillation.

BRIEF DESCRIPTION OF THE DRAWINGS

The invention will now be described in more detail with reference to the attached drawings, in which FIGS. 1 and 1a schematically illustrate the main parts of a defibrillator according to the invention, with the catheter placed in position in a heart indicated schematically, FIG. 1a showing the spacer elements on an enlarged scale.

DETAILED DESCRIPTION OF THE ILLUSTRATED EMBODIMENTS

Figure 1:
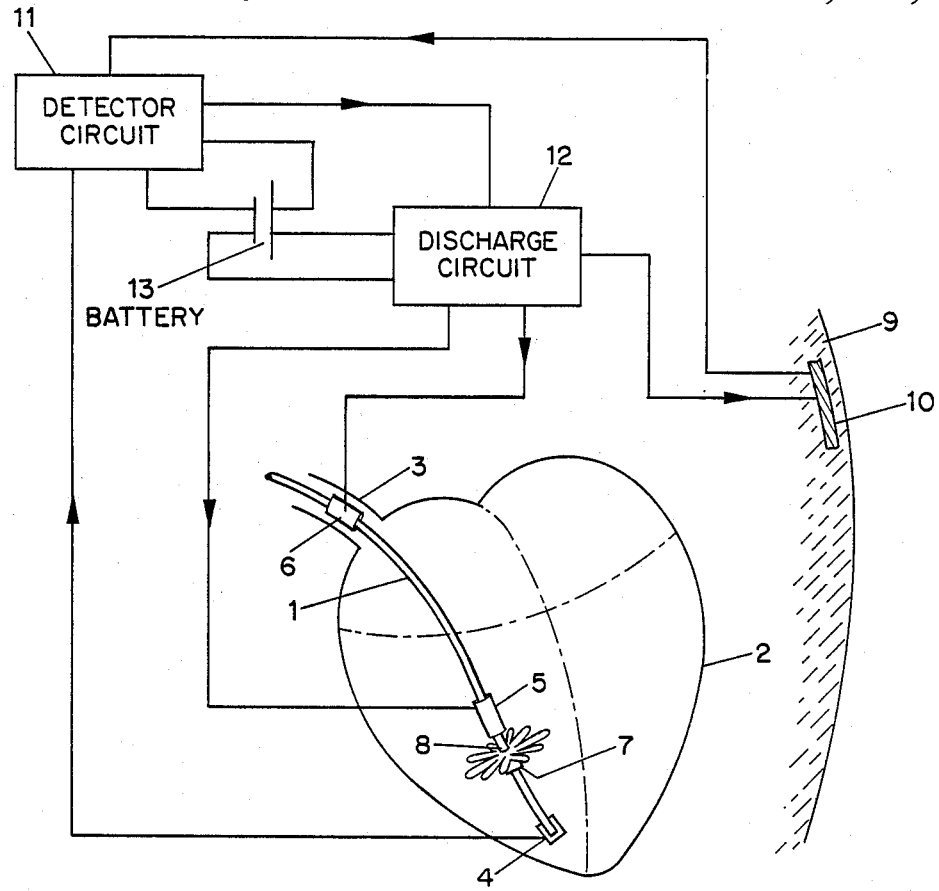
FIG. 1B is a schematic view of a metal box, containing the appropriate control means, battery, and external electrode, and encased within electrically conductive plastic material, so as to be implanted within the patient's body for use as a single unit in lieu of the corresponding separate components shown in FIG. 1.
FIG. 1C is a schematic view of a substantially rigid external electrode which is metallized upon at least one surface thereof.
FIG. 1D is a schematic view of a pair of external electrodes which are connected together by means of a spark gap or surge arrester for use in a system such as that shown in FIG. 4.
FIG. 1E is a schematic view of a flexible external electrode comprising a metal plate encased within electrically conductive plastic material.
Figure 1A:
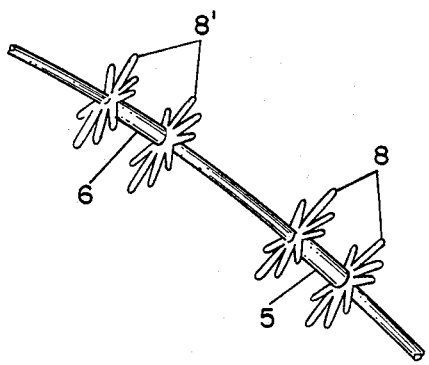
Figure 1C:
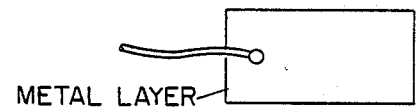
Figure 1D:
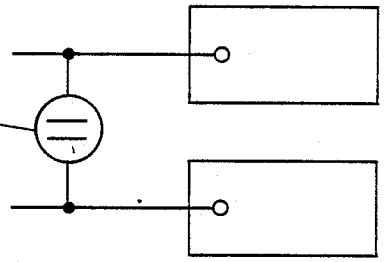
Figure 1B:
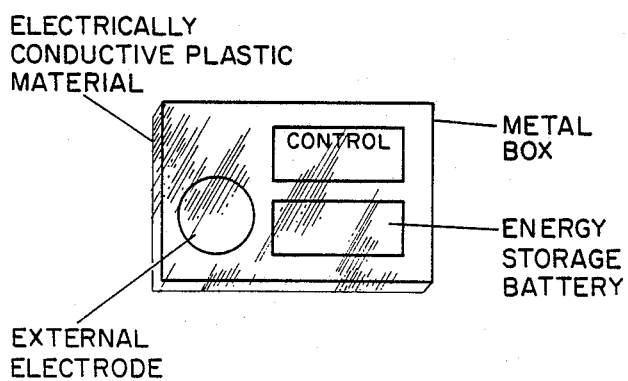
Figure 1E:
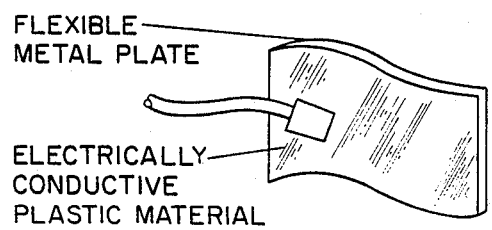

Referring first to FIGS. 1 and 1a, the defibrillator according to the invention comprises a catheter 1, for example of silicone, introduced into the heart 2 through the superior Vena Cava 3. The schematic sketch of FIG. 1 indicates in dash-dot lines the separation of the heart 2 into auricles and ventricles. The catheter 1 is introduced into the right auricle through the Vena Cava 3 and passes from the auricle to the right ventricle. The end of the catheter carries a "second" sensor element 4 which in the case illustrated here consists of a rounded metal cap closing the end of the catheter. The sensor element 4 is situated at the base of the right ventricle, that is to say close to the apex of the heart. Substantially at the level of the middle of the right ventricle, the catheter 1 carries a metal ring 5 which constitutes the first electrode of the apparatus. Substantially at the level of the opening of the Vena Cava into the right auricle, the catheter 1 carries a ring 6 constituting the third electrode of the apparatus. Below the electrode 5, the catheter 1 carries a crown of strips 8 of plastics material resembling a crown of daisy petals in form.

Moulded with the catheter, these petals are naturally substantially perpendicular to the axis of the catheter. When the catheter is introduced into the heart, these petals flexibly fold down on to the catheter. After they have been introduced, they elastically unfold to return to their natural orientation which ensures that the electrode 5 is separated from the wall of the heart. When the catheter is withdrawn, the petals again fold down on the catheter but in the opposite direction.

As may be seen from FIG. 1a, the petals 8 may be placed upstream and/or downstream of the electrode 5. Petals 8' may also be similarly placed upstream and/or downstream of the electrode 6 for the same purpose.

The petals may be detachably mounted on a fixed ring 7 of plastics material or on the catheter.

The subject carries a metal plate 10 formed by a mesh of metal wires as an implant under the skin 9. The plate 10 constitutes the second electrode of the apparatus and at the same time the first element of the sensor. The sensor of the apparatus is thus formed by the two elements 4 and 10. These two elements are connected to a detector circuit 11 which analyzes the electrocardiogram signal. The electrodes 5, 6 and 10 are connected to a discharge circuit 12. The first discharge terminal is connected to the electrode 10 while the other terminal is connected, on the one hand, to the first electrode 5 and on the other hand to the third electrode 6. The circuits 11 and 12 are supplied from a battery 13.

The sensor which registers the signal corresponding to cardiac functioning is composed of the elements 4 and 10. If the detector circuit 11 establishes, from the information supplied by these two elements, that the heart 2 is in a state of ventricular fibrillation, it sends a control signal to the discharge circuit 12 which then transmits a discharge of about 25 joules between the electrodes 5 and 10 at a voltage of from 1000 to 3000 volts. This discharge is sufficient to bring about defibrillation. If, on the other hand, the circuit 11 establishes that the heart 2 is in a state of ventricular tachycardia, it transmits to the circuit 12 a control signal which causes the circuit 12 to transmit a discharge of about 1 joule between the electrodes 5 and the electrode 6 at a voltage of about 400 volts. This discharge, which is preferentially synchronized, is normally sufficient to abolish the state of ventricular tachycardia. If, however, the discharge is not sufficient or if the tachycardia changes into a state of ventricular fibrillation, then the apparatus will automatically deliver a shock of 25 joules between the electrodes 5 and 10.

Since the endocavitory element 4 of the sensor is at some distance from the cells situated in the vicinity of discharge electrode 5, the information provided by the sensor will always faithfully reflect the true functioning of the heart 2.

The distribution of current flow lines during the discharge for defibrillation covers the whole cardiac mass since the second electrode 10, which is the inert electrode, is sufficiently far removed from the heart to ensure that there will be no preferential direction of the flow lines, and since, moreover, the element 8 keeps the electrode 5 within the right ventricle away from any contact with the heart wall. The discharge between the electrodes 5 and 6 in the event of ventricular tachycardia is sufficiently strong to affect the whole mass of the heart in spite of the preferential distribution of the lines of current flow between the electrodes 5 and 6 on the right side of the heart.

The embodiment described above is, of course, in no way limiting and may give rise to any suitable modifications without thereby departing from the scope of the invention. In particular, the electrode 10 may be replaced by the metal box containing the circuits 11,12 and battery 13, this box being implanted inside the body of the subject, for example in the abdominal cavity.

The metal box may be enclosed by, in particular covered with a plastics material or the like filled with an electrically conductive substance, for example silicone filled with metal particles.

The flexible metal plate forming the second, inert discharge electrode may also be enclosed by, in particular covered with a plastics material or the like filled with an electrically conductive substance.

The plastics material is in these two cases in contact with the metal surface of the box and transmits the electric charges to the box. The electric charges can easily circulate over the metal surface of the box which in that case functions as collector of electric charges.

According to another possible embodiment of the inert electrode, this electrode is directly produced in the living tissue. For this purpose, a colloidal solution composed of a physiological solution which holds a biocompatible metal powder, for example of gold or titanium, in colloidal suspension, is injected into a zone of living tissue. This solution diffuses into the tissue and causes the metal powder to be deposited in a predetermined zone of the tissue. This zone becomes electrically highly conductive due to the metal particles which stay in this zone while the supporting solution is removed. The connection to this zone of living tissue is made either by a small rod or plate or sheet of metal implanted in this zone of tissue or by an electrode introduced into a vessel irrigating this zone of tissue.

The second, inert discharge electrode may consist of a film of paper or plastics, in particular polyester, metallized on at least one side.

According to another possibility, a second, inert discharge electrode may be formed from carbon fibres.

It should be noted that the second element 4 of the sensor, which is placed at the end of the catheter 1, may be used to stimulate the heart. This is advantageous since the adjacent tissues are not subject to an elevation of the stimulation threshold, as are the tissues at the level of the discharge electrode 5. The stimulation may be of any nature, to combat bradycardia or tachycardia.

It should also be understood that the whole arrangement preferably constitutes an apparatus which is completely implanted and automatic although all or part of the principles described may be suitable for devices which are not completely implanted and/or not automatic. In particular, for example, the system of electrodes described may be used in intensive care units, the catheter being then introduced into the heart at one end although its other end is passed through the skin to be connected to an external apparatus delivering the shocks or impulses. In that case, the inert electrode or electrodes, instead of being placed under the skin, may be placed on the skin in the form of metal plates without the advantages of the invention being thereby modified.

Furthermore, one could envisage a system similar to that which constitutes the object of the present invention but without automatically releasing the shocks or certain types of the shocks which it is capable of delivering. In fact, the apparatus may be designed to be telecontrolled by telemetry through the skin by a physician who then has the responsibility of deciding when to deliver such a shock and who can then follow the consequences.

Another particular embodiment relates to the detector circuits designed to take the decision for each of the treatments provided. This method consists of recording and analyzing separately the signals produced in the ventricle on electrode 4 and in the auricle on electrode 6 and comparing the times of occurrence of the respective activities. By noting the frequency of each signal and the existence or of absence of synchronism between the two, the apparatus can distinguish between the different types of disturbance and decide on the appropriate treatments to be applied.

Figure 2:
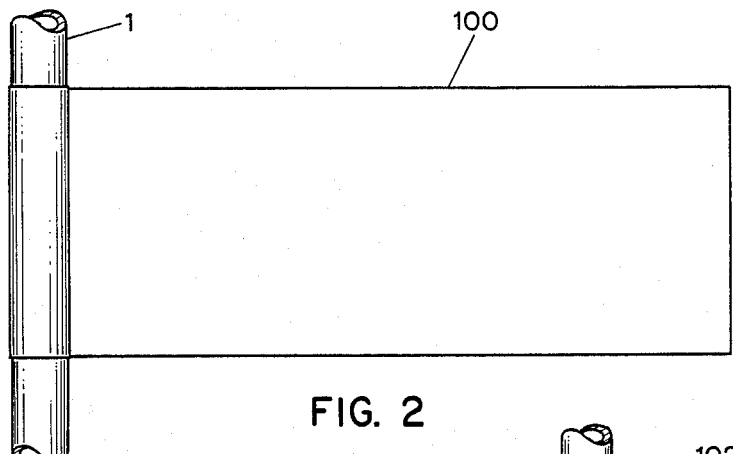
FIGS. 2 and 2a represent an elastic insulating element according to the invention before and after it has been rolled up.
Figure 2A:
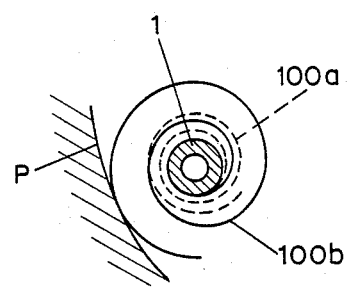

Referring now to FIGS. 2 and 2a, an elastic element 100 functioning as spacer element associated with the ring shaped electrode 5 in the same manner as the spacer element 8 previously described is attached to the catheter 1. This element 100 has the form of an elongated rectangular band attached by one of its short sides to the catheter 1. The surface of this element is very much larger than the lateral surface of the ring 5. According to the invention, this band is wrapped round itself in the form of a spiral and is made of a preformed semi-elastic plastics material so that when the turns of the spiral are released in the right ventricle they partly expand to move from the tightly wound position 100a to the expanded position 100b so that they come into contact with the cardiac wall P. The electrode ring 5 is then effectively separated from the wall P, which is essential for the defibrillation apparatus described above.

Figure 3:
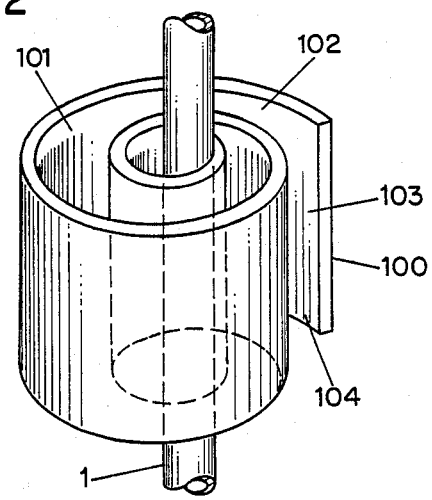
FIG. 3 is a perspective view of an electrode forming part of the elastic element of FIG. 2 rolled up in a spiral which is unwinding.
Figure 4:
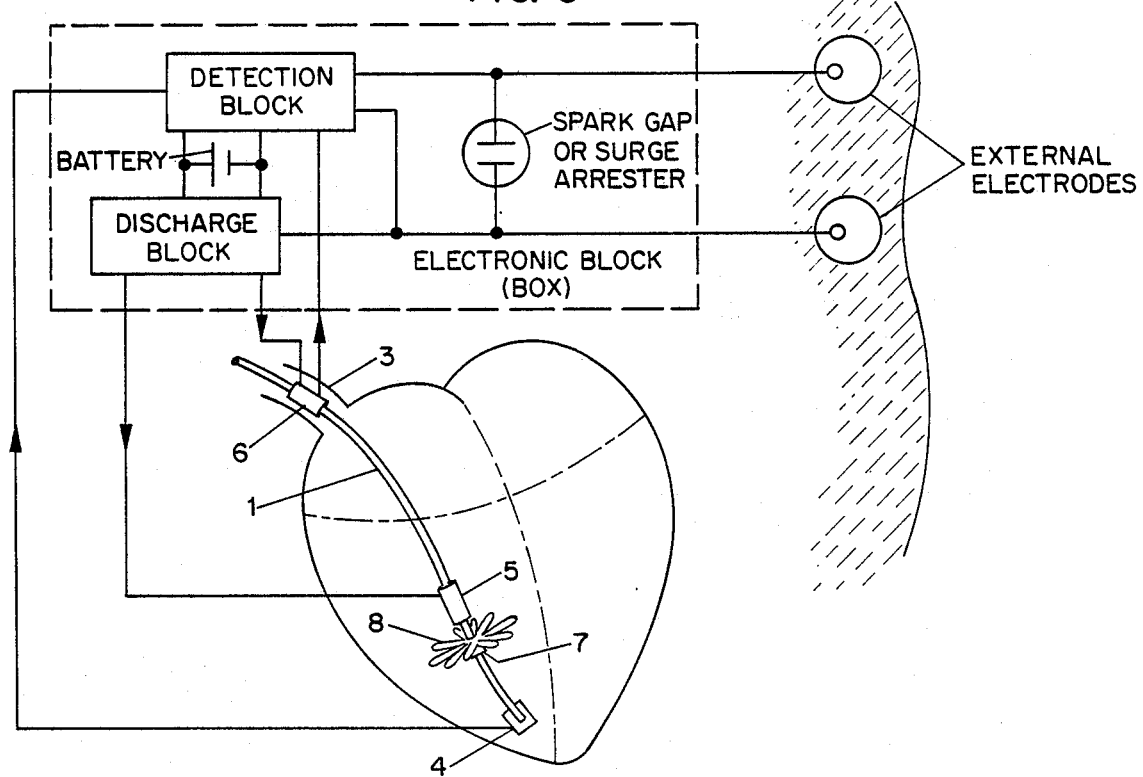
FIG. 4 is a view similar to that of FIG. 1, showing, however, another embodiment of the present invention wherein, in lieu of a single skin-implanted external electrode, a pair of skin-implanted external electrodes, separated by means of a spark gap or surge arrester, as shown in FIG. 1D; are employed.

According to one interesting embodiment of the invention illustrated in FIG. 3 in the expanded position, the same element 100' functions both as electrode and as spacer element. For this purpose, a metal layer 101 is deposited on the internal surface of the spiral band 100'. This layer preferably does not extend right to the edge of the band 100' but leaves a non-conductive zone at its three free edges 102, 103 and 104. According to one variation, this non-conductive zone may be obtained by covering the appropriate portion of band 100' with a fine strip of insulating material folded up and glued down on each side.

When this arrangement is introduced into the right ventricle, the spiral band 100' is tightly held against the catheter by a removable tube. Once the band is in position, this tube is withdrawn and the spirally wound band expands, the non-metallized, external surface of the band functioning as spacer element which insulates the system mechanically and electrically. Withdrawal of the band may be achieved either by virtue of the elasticity of the material at the thickness used for fabricating the band or by slightly bevelling the band on one of its long sides to enable the band to be wound up by rotation of the catheter.

This new type of electrode provides a combination of advantageous features which complement its simplicity of construction and use.

Its design alone enables it to dispose over a large surface area of electrode which can be varied as desired both in magnitude and in distribution. Thus the metallization may cover a greater or smaller part of the surface of the band and/or it may be reinforced in the region where it is electrically connected to the catheter or at the centre so that it functions as charge collector or it may be reduced at the edges.

I claim:

1. A device for delivering a defibrillating or cardioverting electric shock to a patient with recurrent cardiac tachyarrhythmias, comprising:
   a catheter of insulating material and having a distal end for insertion through the right atrium and into the right ventricle of said patient's heart;
   sensor means for sensing the rhythm of the patient's heart beat and transmitting internal cardiac signals corresponding thereto, said sensor means being mounted on said distal end of said catheter;
   at least one discharge electrode for discharging electric current including a first discharge electrode being mounted on said catheter at a first distance from said distal end of said catheter to lie in the right ventricle of said patient's heart away from the interior surface of the heart wall;
   exterior electrode means fitted for sensing the rhythm of the patient's heart beat and creating external and external to internal cardiac sigansl corresponding thereto, and for discharging electric current between said external electrodes and at least one of the internal electrodes in order to perform electrical defibrillation or cardioversion;
   control means including energy means for providing cardioverting or defibrillating energy, and conductor means for operably connecting said sensor means, said discharge electrodes and said exterior electrode means to said control means, said control means including means for receiving said internal and external cardiac signals through said conductor means and means for transmitting, through said conductor means to said exterior electrode means and said first discharge electrode, upon determining a state of ventricular tachycardia or fibrillation, either said cardioverting or defibrillation energy to deliver, respectively, a cardioverting or defibrillating electrical shock.

2. A device for delivering a defibrillating or cardioverting electric shock to a patient with recurrent cardiac tachyarrhythmias, comprising:
   a catheter of insulating material and having a distal end for insertion through the right atrium and into the right ventricle of said patient's heart;
   sensor means for sensing the rhythm of the patient's heart beat and transmitting internal cardiac signals corresponding thereto, said sensor means being mounted on said distal end of said catheter;
   at least one discharge electrode for discharging electric current including a first discharge electrode being mounted on said catheter at a first distance from said distal end of said catheter to lie in the right ventricle of said patient's heart;
   spacing means mounted on said catheter for spacing said first discharge electrode from the interior surface of the heart wall;
   exterior electrode means fitted for sensing the rhythm of the patient's heart beat and creating external and external to internal cardiac signals corresponding thereto, and for discharging electric current between said external electrodes and at least one of the internal electrodes in order to perform electrical defibrillation or cardioversion;
   control means including energy means for providing cardioverting or defibrillating energy, and conductor means for operably connecting said sensor means, said discharge electrodes and said exterior electrode means to said control means, said control means including means for receiving said internal and external cardiac signals through said conductor means and means for transmitting, through said conductor means to said exterior electrode means and said first discharge electrode, upon determining a state of ventricular tachycardia or fibrillation, either said cardioverting or defibrillation energy to deliver, respectively, a cardioverting or defibrillating electrical shock.

3. The device of claim 1 or 2, wherein a second discharge electrode is mounted on said catheter at a second distance greater than said first distance from said distal end such that it is adapted to lie in the right atrium or superior vena cava of the patient's heart, and wherein said control means is further adapted, upon determining a state of ventricular tachycardia, to transmit an electrical discharge between the first and second discharge electrode to correct said ventricular tachycardia.

4. The device of claim 2 wherein said spacing means comprises a crown of radial petals mounted on said catheter at a position directly adjacent to said first discharge electrode such that said crown lies in the right ventricle of said patient's heart, said petals being angularly directed from the catheter axis so that said petals space said first discharge electrode from the interior surface of the heart wall and are elastically collapsible toward the axis to allow the introduction or extraction of said catheter into or from the patient's heart.

5. The device of claim 3 wherein said exterior electrode means includes at least two exterior electrodes, at least one of which both senses the rhythm of the patient's heart and discharge electric current.

6. The device of claim 5 further including at least one spark gap element disposed between at least two of said exterior electrodes to provide an electrical connection therebetween 7. The device of claim 1 or 2, wherein said exterior electrode means comprises a metal box for containing said control means.

8. The device of claim 7, further including an electrically conductive plastic material enclosing said metal box.

9. The device of claim 1 or 2, wherein said exterior electrode means comprises a flexible metal plate.

10. The device of claim 9 further including an electrically conductive plastic material enclosing said flexible metal plate.

11. The device of claim 1 or 2, wherein said exterior electrode means comprises a plastic material which is metallized on at least one side.

12. The device of claim 1 or 2, wherein said exterior electrode means comprises carbon fibers.

13. The device of claim 1 or 2, wherein said sensor means includes means for stimulating the heart.

14. The device of claim 2 wherein said spacing means comprises an elongated ribbon mounted on and wound around said catheter so that when unwound said ribbon contacts the heart wall to space said first discharge electrode from the interior surface of said heart wall.

15. The device of claim 14 wherein said elongated ribbon includes an internal and exterior surface wherein at least one of said surfaces is metallized.

16. The device of claim 15 wherein said metallized surface includes at least one non-metallized strip along the periphery of said surface.

17. The device of claim 16 wherein said metallized surface further includes a plurality of re-enforced metallization areas.

18. A cardiac defibrillator for delivering a defibrillating or cardioverting electric shock to a patient with recurrent cardiac tachyarrhythmias, comprising:
a catheter of insulating material and having a distal end, said catheter for insertion through the right atrium and into the right ventricle of a patient's heart;
a pluraity of electrodes including at least one exterior electrode and including a first discharge electrode being mounted on said catheter at a first distance from said distal end of said catheter to lie in the right ventricle of said patient's heart;
spacer means for spacing said first discharge electrode from the interior surface of the heart wall; and
control means including energy means for providing cardioverting or defibrillating energy; and conductor means for operably connecting said electrodes to said control means, said control means further including means for transmitting said energy to deliver respectively, through said conductor means to said exterior and first discharge electrodes a cardioverting or defibrillating electrical shock.

19. The device of claim 18, wherein a second discharge electrode is mounted on said catheter at a second distance greater than said first distance from said distal end of said catheter to lie in the right atrium or superior vena cava of the patient's heart, and wherein said control means further includes means for transmitting said energy to deliver, respectively, through said conductor means to said first and second discharge electrode, upon determining a state of ventricular tachycardia, an electrical discharge between the first and second electrode to correct said ventricular tachycardia.

20. The device of claim 18, further including sensor means mounted on the catheter at a second distance greater than said first distance from said distal end to lie in the right atrium or superior vena cava of the patient's heart, and wherein said conductor means further operably connects said exterior electrode and said sensor means to said control means, and wherein said control means further includes means for receiving internal and external cardiac signals transmitted by said sensor means and said exterior electrode, respectively, and means for transmitting said energy to delivery, respectively, through said conductor means to said exterior electrode and said first discharge electrode, upon determining a state of ventricular tachycardia or fibrillation, a cardioverting or defibrillating electrical shock.

21. The device of claim 20, wherein said sensor means further includes means for discharging electric current, and wherein said control means further including means for transmitting said energy to deliver through said conductor means to said first electrode and sensor means, upon determining a state of ventricular tachycardia, and electrical discharge between the first electrode and sensor means to correct said ventricular tachycardia.

22. The device of claim 18, further including sensor means for sensing the rhythm of the patient's heart beat and transmitting cardiac signals corresponding thereto, said sensor means having at least two elements each being mounted on said catheter, at least two to lie, respectively, in the right ventricle and in the right atria of the patient's heart and wherein said control means uses the time comparison of the cardiac signals for detecting cardiac disorders.

23. A device for delivering a defibrillating or cardioverting electric shock to a patient with recurrent cardiac tachyarrhythmias, comprising:
a catheter of insulating material and having a distal end for insertion through the right atrium and into the right ventricle of a patient's heart;
a plurality of discharge electrodes including a first discharge metallic ring shaped electrode being mounted on said catheter at a first distance from said distal end of said catheter to lie in the right ventricle of said patient's heart;
spacing means mounted on said catheter for spacing said first discharge electrode from the interior surface of the heart wall.

* * * * *